(12) United States Patent
Tassoni et al.

(10) Patent No.: US 10,631,869 B2
(45) Date of Patent: Apr. 28, 2020

(54) PUSHER ARM AND BALL RELEASE MECHANISM FOR EMBOLIC COILS

(71) Applicant: Boston Scientific Scimed, Inc., Maple Grove, MN (US)

(72) Inventors: Nicholas Tassoni, Andover, MA (US); Mary-Claire Anderson, Minneapolis, MN (US); Gary Pederson, Albertville, MN (US); Ken Zhang, Maple Grove, MN (US); Martin R Willard, Burnsville, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 638 days.

(21) Appl. No.: 15/286,985

(22) Filed: Oct. 6, 2016

(65) Prior Publication Data
US 2017/0095258 A1 Apr. 6, 2017

Related U.S. Application Data

(60) Provisional application No. 62/237,904, filed on Oct. 6, 2015.

(51) Int. Cl.
*A61B 17/12* (2006.01)
(52) U.S. Cl.
CPC .... *A61B 17/12145* (2013.01); *A61B 17/1214* (2013.01); *A61B 17/12031* (2013.01); *A61B 2017/12054* (2013.01)

(58) Field of Classification Search
CPC ........ A61B 17/12109; A61B 17/12131; A61B 17/1214; A61B 2017/12054
See application file for complete search history.

(56) References Cited

U.S. PATENT DOCUMENTS

| 5,350,397 | A | | 9/1994 | Palermo et al. |
| 5,895,391 | A | * | 4/1999 | Farnholtz ......... A61B 17/12022 606/108 |
| 5,925,059 | A | * | 7/1999 | Palermo ........... A61B 17/12022 606/191 |
| 2009/0036877 | A1 | | 2/2009 | Nardone et al. |
| 2012/0041470 | A1 | | 2/2012 | Shrivastava et al. |
| 2013/0138136 | A1 | | 5/2013 | Beckham et al. |
| 2014/0058434 | A1 | | 2/2014 | Jones et al. |
| 2014/0058435 | A1 | * | 2/2014 | Jones ................ A61B 17/1214 606/200 |

\* cited by examiner

*Primary Examiner* — Shaun L David
*Assistant Examiner* — Christina C Lauer

(57) ABSTRACT

This disclosure concerns release mechanisms for medical implants, particularly embolic coils and the like, which utilize bulbous elements and receiving elements to constrain the bulbous elements. In some cases, the receiving elements are sized and shaped to help constrain the bulbous element axially and/or radially, and may work in concert with constraining elements and/or release wires that are optionally moveable independently of the receiving elements.

15 Claims, 5 Drawing Sheets

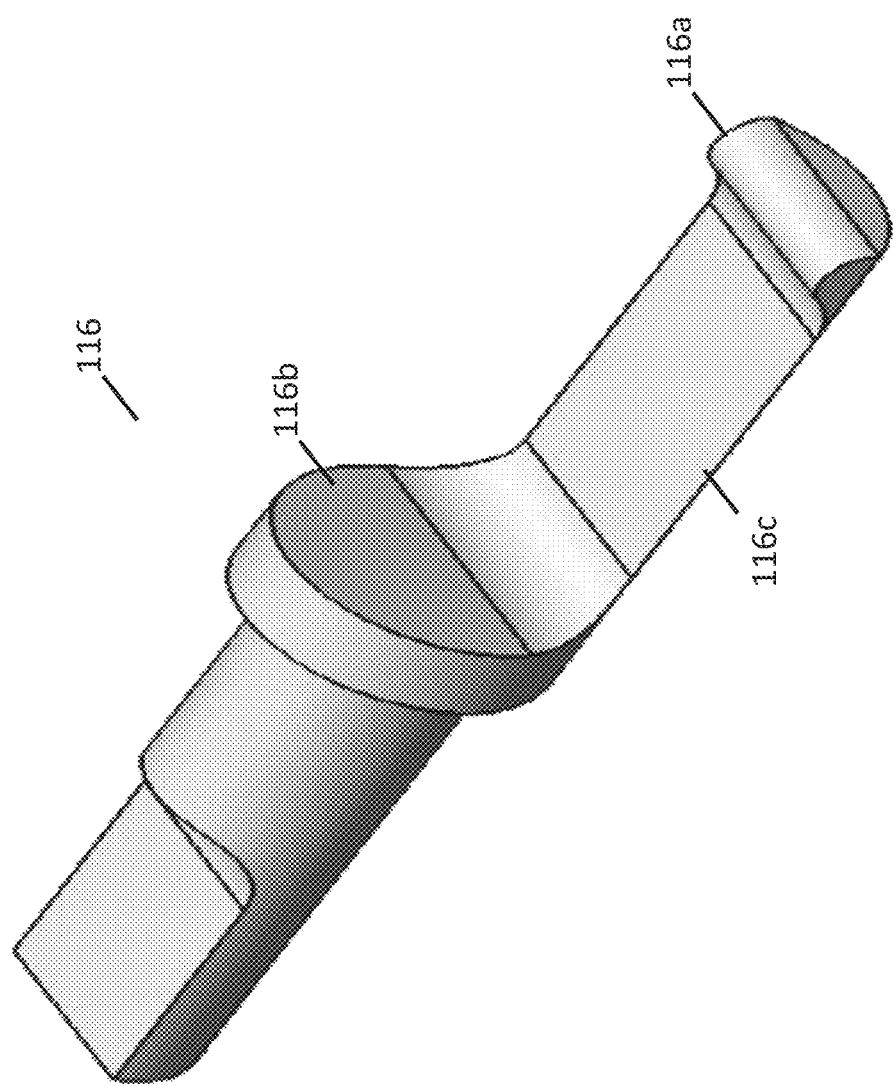

PUSHER ARM AND BALL RELEASE MECHANISM FOR EMBOLIC COILS

PRIORITY

This application claims the benefit of priority under 35 U.S.C. § 119 to U.S. Provisional Patent Application Ser. No. 62/237,904, filed Oct. 6, 2015, which is incorporated by reference in its entirety and for all purposes.

FIELD OF THE INVENTION

This application relates to the field of medical devices and medical procedures. More particularly, the application is related to devices and methods for occluding body lumens such as blood vessels.

BACKGROUND

Therapeutic embolization or occlusion of blood vessels may be used to treat a variety of vascular and non-vascular conditions including cerebral and peripheral aneurysms, arteriovenous malformation, uterine fibroids and various tumors. One commonly used agent for embolizing blood vessels is the embolic coil, a permanently implanted coiled wire structure which, when implanted into a blood vessel, occludes the vessel by causing thrombosis where it is deployed. Embolic coils may have different lengths and/or cross-sectional diameters, in order to fit into and occlude vascular structures of varying sizes. In use, the coils are delivered through a microcatheter in a narrow-diameter elongated configuration (e.g. to fit within a 3 Fr catheter lumen). Once deployed into the vessel, the coil may assume a complex 3-D shape such as a helix, a spiral, a J-shape, or a birds-nest shape, and may include thrombogenic fibers or bundles of fibers along its length. Embolic coils are highly flexible, and can be delivered through narrow or tortuous vascular structures, but when occlusion of relatively large vascular structures is desired, multiple coils may be necessary to achieve full occlusion.

These coils have typically been placed at the desired site using a catheter and a pusher. The site is first accessed by the catheter. In treating peripheral or neural conditions requiring occlusion, the sites are accessed with flexible, small diameter catheters, which may be guided to the site through the use of guidewires and/or flow-directed means such as balloons at the distal end of the catheter. Once the site has been accessed, the catheter lumen is cleared (i.e., the guidewire is removed if a guidewire has been used), and the coil is placed in the proximal end of the catheter and advanced through the catheter with a pusher. When the coil reaches the distal end of the catheter it is advanced into the vessel and deployed. This technique of plunging the coil from the distal end of the catheter has undesirable limitations. First, because of the plunging action of the pusher during deployment, the positioning of the coil at the site cannot be controlled to a fine degree of accuracy. Second, once plunged from the catheter, it is difficult to reposition or retrieve the coil if desired. Indeed, another device, called a retriever, must be threaded through the catheter to snare the coil to reposition or retrieve it.

The coil is typically connected to the pusher or another structure within the catheter and must be detached. This detachment is typically facilitated by the use of an electrolytically severable link or a mechanical coupling. While current detachment mechanisms are generally reliable, they may not release the coil when triggered 100% of the time. In the case of mechanical detachment mechanisms in particular, improving detachment reliability may involve undesirable trade-offs such as increasing the size and/or cost of parts used in detachment mechanisms.

SUMMARY OF THE INVENTION

The present invention, in its various aspects, provides improved mechanical coil detach systems which achieve 100% detachment and which minimize the trade-offs between 100% detachment and increased size and/or expense.

In one aspect, the present invention relates to a system for treating a patient which includes a catheter defining a lumen, a pusher assembly slidably disposed within the lumen, a constraining element slidably disposed within the lumen and moveable independently of the pusher assembly, which constraining element has a tubular distal end disposable about a distal portion of the pusher assembly, and an embolic coil with a proximal end comprising a bulbous element. The pusher assembly, in preferred embodiments, includes a distal receiving element having a first portion defining a first planar surface extending radially and a second portion defining an elongated planar surface extending substantially perpendicular to and distally from the planar surface, the elongated planar surface having a protrusion extending away from the planar surface. In some embodiments, the inner diameter of the tubular distal end of the constraining element is closely toleranced to the combined outer diameter of the bulbous element of the embolic coil and the second portion of the distal receiving element (for instance, the inner diameter is, in some cases, not more than 133% of (a) an outer diameter of the bulbous element of the embolic coil, plus (b) a thickness of the second portion of the distal receiving element). Similarly, in some embodiments, the protrusion extends a distance from the elongated planar surface that is less than 50% of a diameter of the bulbous element. More generally, in certain embodiments, the combination (i.e. the combined thickness) of the extension of the protrusion from the elongated planar surface and the second portion of the distal receiving element is greater than or equal to a difference between the inner diameter of the tubular distal end of the constraining element and the combined outer diameter of the bulbous element of the embolic coil and the second portion of the distal receiving element. In some cases, the bulbous element is connected to the embolic coil by one of a wire and a rod extending axially along a central axis of the coil, and wherein the wire or rod extends axially along a central axis of the embolic coil when the bulbous element and receiving element are engaged and disposed within the lumen of the tubular distal end of the constraining element. The constraining element and pusher assembly may be arranged within the lumen in several different ways to permit smooth catheter operation and/or to minimize the potential for mechanical interference between those parts. For instance, in some cases the constraining element includes a wire or a rod disposed proximally of the tubular distal end, the wire or rod extending parallel to the pusher assembly, in which case the pusher assembly is disposed coaxially within the catheter lumen. In other cases, the constraining element includes a coiled segment disposed proximally of the tubular distal end, in which case the pusher assembly is disposed coaxially within a lumen defined by the coiled segment. In still other cases, the constraining element includes a wire or a rod disposed proximally of the tubular distal end and disposed coaxially within the catheter lumen and the pusher assembly includes an elongated portion extending parallel to the wire and through a proximal aperture within the tubular distal end. In various cases, the distal receiving element is a single piece. In preferred cases, the embolic coil is secured to the catheter by contacting the bulbous element and the distal receiving element and advancing the constraining element at least partially over the bulbous element and the distal receiving element and, optionally, the coil is released by moving at least one of the pusher assembly and the constraining element relative to the other. In some cases, the pusher assembly and constraining element can be retracted from the catheter and replaced with a pusher assembly and constraining element engaged with a second embolic coil. The system according to this aspect can be used in medicine, for instance for the treatment of vascular conditions, and can be included in kits for use by medical personnel.

In another aspect, the present invention relates to a system for treating a patient which includes a catheter defining a first lumen, a pusher assembly slidably disposed within the first lumen and having a tubular distal element defining a second lumen, which tubular distal element includes a slot formed in a wall thereof, a release wire slidably disposed within the first lumen and moveable independently of the pusher assembly, and an embolic coil with a proximal end comprising a bulbous element. In various embodiments according to this aspect, the tubular distal end has an inner diameter that is less than a combined diameter of the bulbous element plus a diameter of the release wire, and wherein the release wire is disposable (i.e. it can be positioned) near an inner wall of the tubular distal element opposite the slot so as to displace the bulbous element into the slot. The pusher assembly can include, in some cases, a wire or a rod disposed proximally of the tubular distal end and coaxially within the catheter lumen, in which case the release wire extends parallel to the pusher assembly, or the pusher can include a coiled segment disposed proximally of the tubular distal end, in which case the release wire can be disposed coaxially within a lumen defined by the coiled segment.

In yet another aspect, the present invention relates to a method of treating a patient by inserting into that patient's body a catheter having a pusher assembly, distal receiving element, constraining element and embolic coil with a bulbous element as described above. Once inserted, at least one of the pusher assembly and the constraining element is moved relative to the other, thereby permitting the bulbous element to separate from the distal receiving element. As above, in some cases the inner diameter of the tubular distal end of the constraining element is not more than 133% of the outer diameter of the bulbous element of the embolic coil plus the thickness of the second portion of the distal receiving element, the protrusion extends a distance from the elongated planar surface that is less than 50% of a diameter of the bulbous element, and/or the combination of the extension of the protrusion from the elongated planar surface and the second portion of the distal receiving element is greater than or equal to a difference between the inner diameter of the tubular distal end of the constraining element and the combined outer diameter of the bulbous element of the embolic coil and the second portion of the distal receiving element. The bulbous element can be connected to the embolic coil by one of a wire and a rod extending axially along a central axis of the coil, such that the wire or rod extends axially along a central axis of the embolic coil when the bulbous element and receiving element are engaged and disposed within the lumen of the tubular distal end of the constraining element. The method can also include a step of retracting the pusher assembly, and may also include a step of retracting the constraining element prior to the retraction of the pusher assembly. In some cases, the pusher assembly and the constraining element are withdrawn from the catheter, and a pusher assembly and constraining element engaged with a bulbous element of a second embolic coil is reinserted into the catheter. Finally, in some cases the method includes positioning at least part of the embolic coil within a vascular structure to be occluded.

DRAWINGS

Aspects of the invention are described below with reference to the following drawings in which like numerals reference like elements, and wherein:

FIG. 3 shows a schematic depiction of a receiving element as used in the delivery catheter of FIGS. 1 and 2.

Figure 4A:
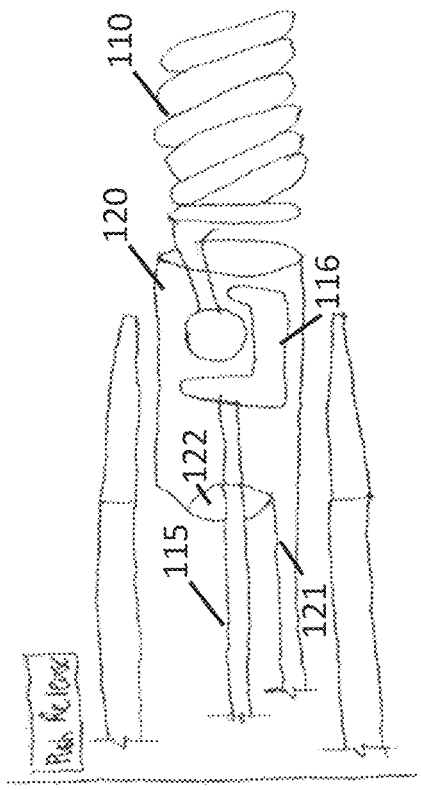

FIGS. 4A, B, C, D, E and F show, in schematic form, various alternative configurations of delivery catheters according to the embodiments of the present invention.

Unless otherwise provided in the following specification, the drawings are not necessarily to scale, with emphasis being placed on illustration of the principles of the invention.

DETAILED DESCRIPTION OF THE PREFERRED EMBODIMENTS

Figure 1:
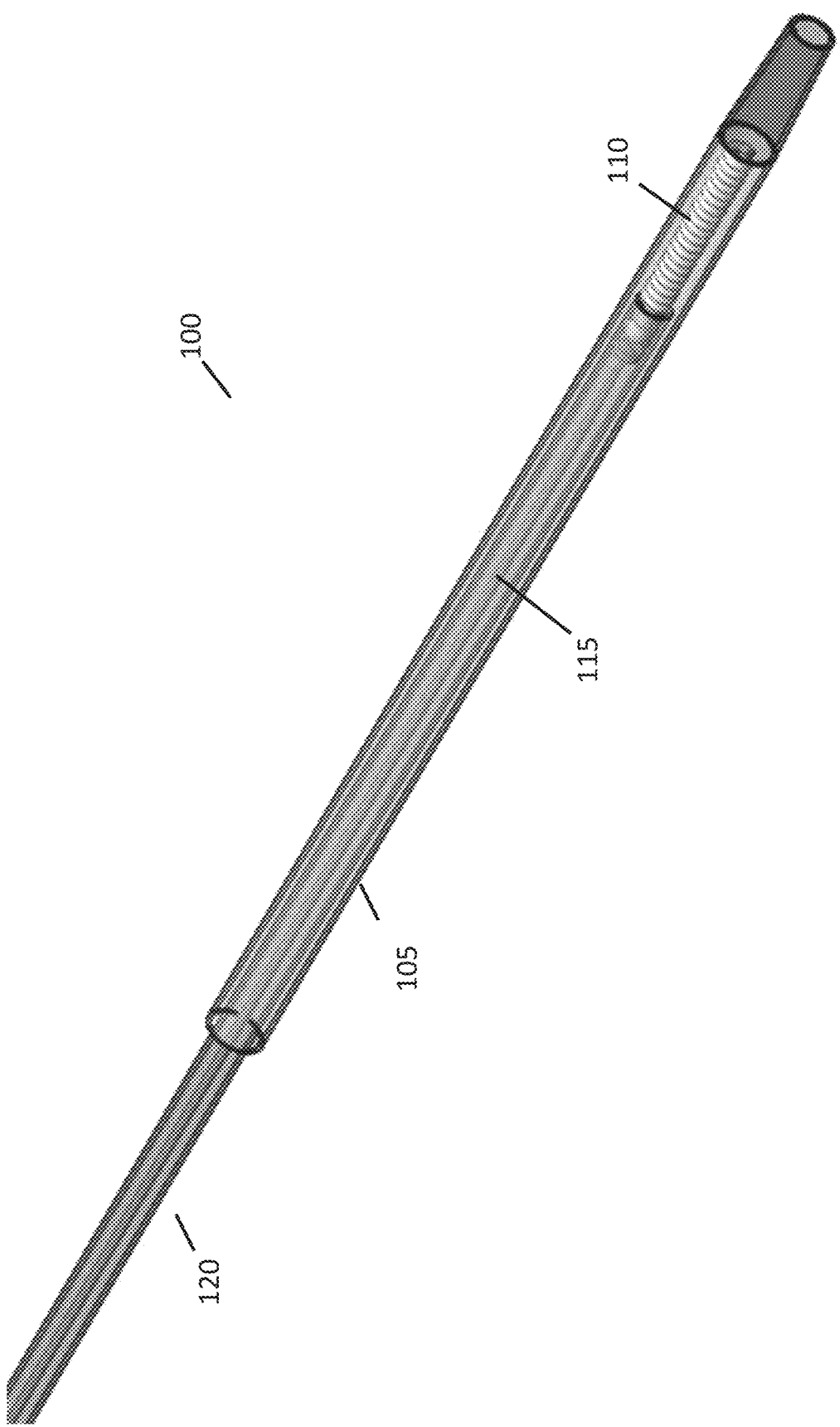
FIG. 1 shows a schematic view of a delivery catheter according to certain embodiments of the present invention.

An exemplary catheter assembly 100, as shown in FIG. 1, includes a generally tubular catheter 105, an embolic coil 110 (though any other implantable medical device of similar size may be used) having, at its proximal end, a ball or other bulbous element 111, a pusher assembly 115 slidably disposed within the catheter 105 and having, at its distal end, a receiving element 116 that is sized to engage the ball 111. The catheter assembly 100 also includes a constraining element 120 that is slidable within the catheter lumen independently of the pusher assembly 115 and which constrains the axial or radial movement of the ball 111 when it is engaged with the receiving element 116.

Figure 2A:
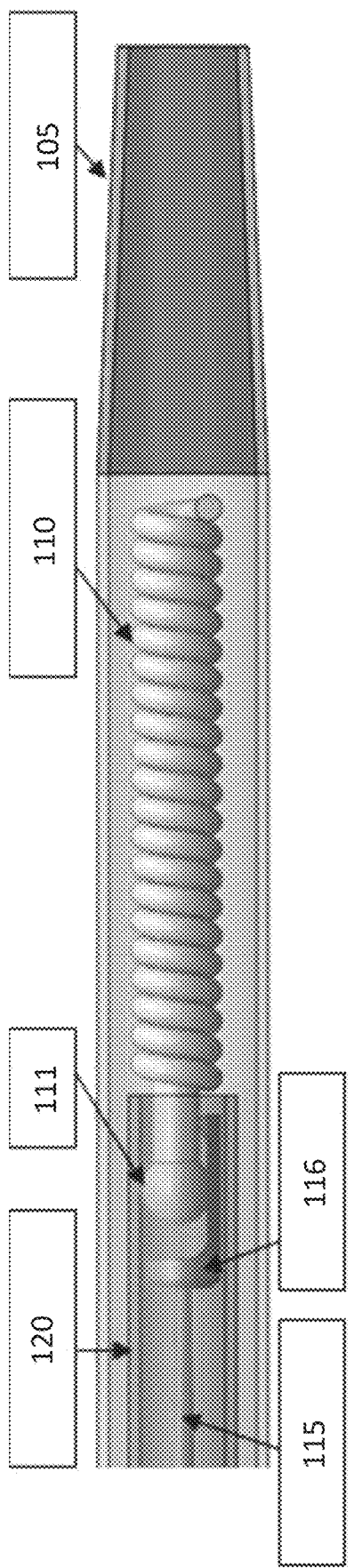
FIGS. 2A, 2B and 2C show schematic views of the catheter of FIG. 1 at three points during the detachment process.

The constraining element 120 depicted in FIGS. 1 and 2 has a generally tubular distal end and has an inner diameter that is slightly larger than the combined width of the ball 111 and the receiving element 115 when the two are engaged (e.g. 10% larger, 20% larger, 30% larger, 40% larger or 50% larger). Together with a lip or ridge 116a on the receiving element, the constraining element 120 helps limit both the axial and radial movement of the ball 111 when it is engaged with the receiving element 116 and is contained within the lumen of the constraining element 120. This arrangement is shown in FIG. 2A and is used to advance the coil 110 through the distal end of the catheter 105.

Figure 2B:
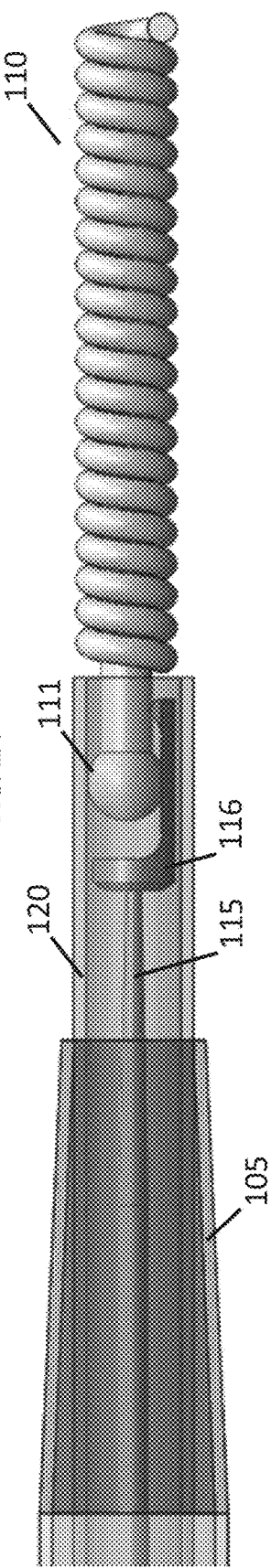
Figure 2C:
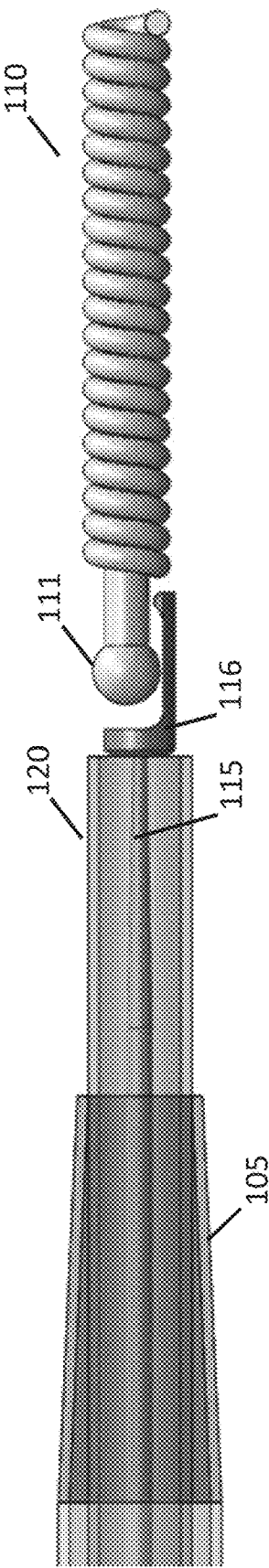

As FIG. 2B illustrates, as the coil 110 is advanced through the distal end of the catheter 105, the constraining element 120 remains positioned over the ball 111 and the receiving element 116 of the pusher assembly 115, permitting the placement of the coil 110 prior to its release. When release of the coil is desired, the constraining element 120 is retracted over the pusher assembly 115 or, alternatively, the pusher assembly 115 is advanced through the constraining element 120; in either case, the ball 111 is exposed (FIG. 2C), thereby releasing the embolic coil 110.

The catheter assembly 100 shown in FIGS. 1 and 2 has several advantageous characteristics, including without limitation the following: it is 100% detachable yet it allows a user to recapture the coil 110 by engaging the receiving element 116 with the ball 111 and advancing the constraining element 120 over both. At the same time, the simple design has a small overall diameter that will tend to preserve the flexibility of the catheter assembly 100 and can be implemented using materials that are currently used to produce delivery catheters.

Turning now to FIG. 3, an exemplary receiving element 116 includes a proximal axially constraining surface 116b and a radially constraining surface 116c which in turn includes, at its distal end, a ridge or lip 116a that serves to further limit the axial movement of the ball 111 and therefore the coil 110 when the constraining element 120 is extended over the ball 111 and the receiving element 116. Each of the proximal axially constraining surface 116b, the radially constraining surface 116c and the lip or ridge 116a are generally continuous with one another (such that the receiving element 116 can be fabricated as a single piece) and preferably have relatively flat (in the case of the radial and axial constraining surface), even surfaces.

The receiving element 116 depicted in FIG. 3 is superficially similar to the design of Engelson disclosed in U.S. Pat. No. 5,261,916 (which is incorporated by reference in its entirety and for all purposes herein), but the skilled artisan will appreciate that Engelson utilizes a pusher with an enlarged cylindrical tip having both an axial bore and a radial slot to receive the ball of the embolic coil, such that the coil is constrained both proximally and distally by a body having a diameter equal to or greater than the diameter of the ball. In the embodiment of FIGS. 1-3, however, the lip 116a is significantly smaller than the diameter of the ball 111. For instance, in one case the ball 111 has a diameter of approximately 0.012" (0.30 mm), while the lip or ridge 116a may have a convex curved surface with a radius of 0.0035" (0.09 mm). More generally, the lip 116a preferably extends a distance that is equal to or, preferably, slightly greater than the difference between the inner diameter of the constraining element 120 and the combined outer diameters of the receiving element 116 and the ball 111 when the two are engaged. This configuration limits radial displacement of the ball 111 and the proximal end of the embolic coil 110 during the delivery process, aiding accurate placement of the coil 110 with a relatively low risk of coil movement during release. At the same time, the distance is not so great as to reduce the mechanical clearance of the ball 111 or the connector between the ball 111 and the coil 110 when it is engaged with the receiving element 116 and the constraining element 120.

While the embodiments presented above exemplify certain aspects of the present invention, it is not limited in scope to those aspects. For instance, the constraining element 120 is depicted throughout FIGS. 1, 2 and 3 as a cylindrical body having constant inner and outer diameters and extending the entire length of the catheter assembly 100. This arrangement has the advantages described above, but the resulting catheter assembly 100 may be comparatively stiff, as the constraining element is preferably robust to deformation or "ovalization" that could potentially allow the ball 111 to migrate during delivery.

Figure 4B:
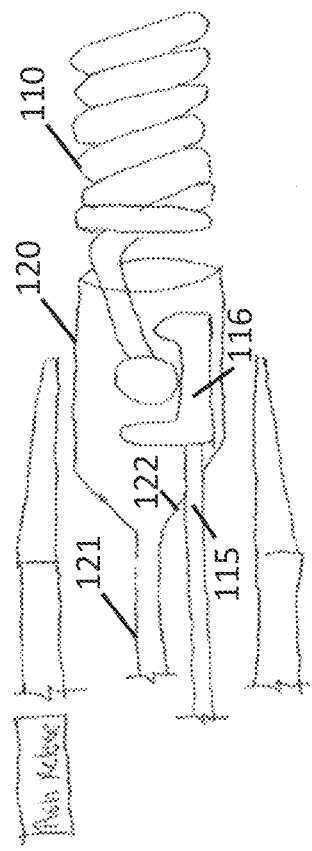

In situations where embolic coils are to be delivered through tortuous and/or narrow diameter vessels, a more flexible catheter may be desired; this is achieved in various embodiments by altering the diameter, length or rigidity of the constraining element 120 along the length of the catheter assembly 100. For instance, in some cases, the diameter of the constraining element 120 is maximized at its distal end so as to encompass the ball 111 and the receiving element 116, then decreases proximally. Alternatively, the distal portion of the constraining element 120 may be made more rigid than the proximal portion (e.g. by means of greater wall thickness, incorporation of a rigid material such as a reinforcing fiber or braid, or a rigid bushing) allowing the distal end to resist ovalization while the proximal end retains flexibility. And, in yet another alternative illustrated in FIGS. 4A-B, the distal constraining element 120 has a length that is significantly less than the length of the catheter 105 and is connected, at its proximal end, to a wire or other structure 121 that enables the constraining element 120 to be pushed or pulled relative to the catheter 105 and/or the pusher assembly 115. In the embodiments shown in FIGS. 1-3, the constraining element 120 and the pusher assembly are arranged coaxially (i.e. the pusher assembly 115 is centered) along substantially all of the length of the catheter assembly 100; in the embodiment of FIG. 4A, the wire 121 is centered, and the constraining element includes an off-center proximal aperture 122 to accommodate the pusher assembly 115. Alternatively, if the pusher assembly 115 is centered, the proximal aperture 122 is located more centrally, while the wire 121 is off-center as shown in FIG. 4B.

In addition to improved flexibility, the relatively short constraining element 120 shown in FIGS. 4A-B, as well the embodiments described below, facilitate of fluid injection through the delivery catheter 105: the use of a tubular constraining element 120 of relatively short length may reduce the fluid pressure necessary to inject fluid through the catheter 105, by providing a comparatively larger inner diameter across most of its length. By contrast, the diameter of the lumen available for fluid flow is reduced along the entire length of the catheter 105 when the constraining element 120 is a tube extending the entire length of the catheter 105.

Embolic coil 110 will, in certain embodiments, have both a primary helical structure and a complex secondary structure, such as a helix, an ovoid shape, a J-shape, etc., as described in U.S. Pat. No. 5,639,277 to Mariant, et al, which is incorporated by reference herein for all purposes. Because the coil 110 tends to assume the secondary shape when unconstrained, it may expand while disposed within the lumen of the catheter 105 and, as the coil 110 is advanced through the catheter 105, it may tend to twist. One potential complication of the designs of FIGS. 4A-B, and those described below, is that this twisting may cause the wire 121 to twist, potentially twisting around the pusher assembly 115. In order to prevent twisting of the wire 121 and the pusher assembly 115, the catheter optionally includes constraining elements such as small bushings, or wire rings, which limit the circumferential and/or radial movement of one or both of the wire 121 and the pusher assembly 115. These wires, bushings, etc. are preferably positioned at multiple places along the length of the catheter 105, thereby ensuring that the wire 121 and the pusher assembly 115 do not mechanically interfere with one another along the length of the catheter 105 during the delivery process.

Figure 4C:
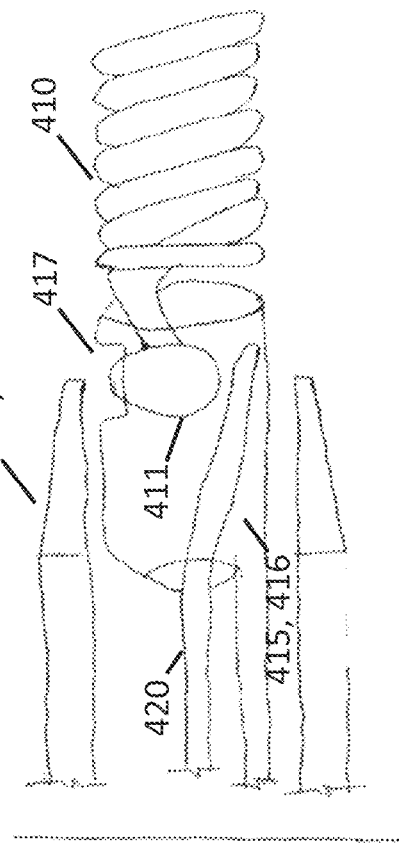
Figure 4D:
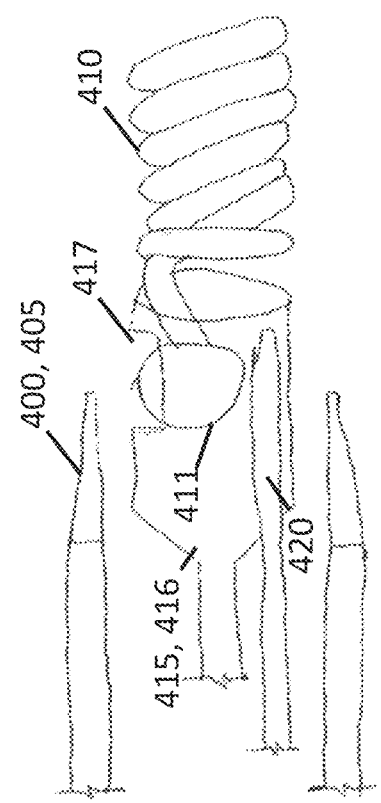

In another group of embodiments, a pusher assembly including a receiving element provides both radial and axial constraint of the ball with the aid of a wire or other narrow body that urges the ball and the receiving element together. For instance, in FIGS. 4C-D, a catheter assembly 400 includes a catheter 405 for delivering an embolic coil 410 having a proximal ball 411, which catheter includes a pusher assembly 415 with a tubular receiving element 416 having an axial bore defining a lumen and a slot 417 cut into the side-wall of the receiving element 416 that is sized to accommodate part or all of the ball 111. The assembly also includes a release wire 420 slidably disposed in the catheter 405 that is independent of the pusher assembly 415. The release wire 420 is positioned to urge the ball 411 toward the slot 417, providing axial and radial constraint of the ball 411 during delivery. As discussed above, either the pusher assembly 415 or the release wire 420 can be centered, in which case the other is off-center. In either case, the release wire 420 and the pusher assembly 415 are optionally constrained to prevent tangling or crossing at one or more points along the length of the catheter 405, for instance by one or more wire rings, or by the use of a guidewire lumen or slit within the catheter 405 (not shown).

In use, the catheter assembly 400 operates by "pull release": in order to deploy the coil 410, the pusher assembly 415 and the release wire 420 are advanced distally relative to the catheter 405; once the coil is suitably positioned, the release wire 420 is retracted proximally, thereby releasing the coil 410.

Figure 4F:
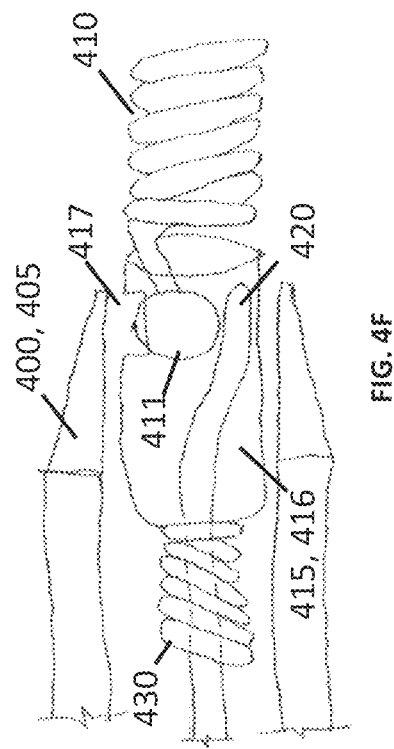
Figure 4E:
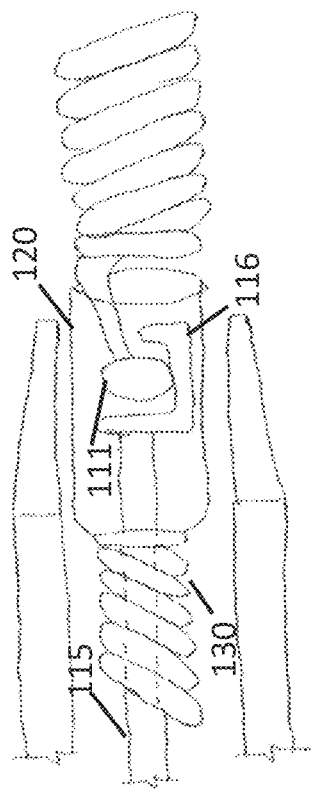

Turning now to FIGS. 4E-F, in some cases, the pusher assembly and constraining element are arranged coaxially, with the pusher element 115 being central and extending through a hollow central portion 130 of the constraining element 120 (FIG. 4E). Alternatively, as shown in FIG. 4F, the release wire 420 can extend through a hollow central portion 430 of the pusher assembly 416. The hollow central portion 130 430 can be a coil or other suitable hollow body through which the pusher assembly 115 or the release wire 420, respectively, is be slidably disposed.

The phrase "and/or," as used herein should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

The term "consists essentially of" means excluding other materials that contribute to function, unless otherwise defined herein. Nonetheless, such other materials may be present, collectively or individually, in trace amounts.

As used in this specification, the term "substantially" or "approximately" means plus or minus 10% (e.g., by weight or by volume), and in some embodiments, plus or minus 5%. Reference throughout this specification to "one example," "an example," "one embodiment," or "an embodiment" means that a particular feature, structure, or characteristic described in connection with the example is included in at least one example of the present technology. Thus, the occurrences of the phrases "in one example," "in an example," "one embodiment," or "an embodiment" in various places throughout this specification are not necessarily all referring to the same example. Furthermore, the particular features, structures, routines, steps, or characteristics may be combined in any suitable manner in one or more examples of the technology. The headings provided herein are for convenience only and are not intended to limit or interpret the scope or meaning of the claimed technology.

Certain embodiments of the present invention have been described above. It is, however, expressly noted that the present invention is not limited to those embodiments, but rather the intention is that additions and modifications to what was expressly described herein are also included within the scope of the invention. Moreover, it is to be understood that the features of the various embodiments described herein were not mutually exclusive and can exist in various combinations and permutations, even if such combinations or permutations were not made express herein, without departing from the spirit and scope of the invention. In fact, variations, modifications, and other implementations of what was described herein will occur to those of ordinary skill in the art without departing from the spirit and the scope of the invention. As such, the invention is not to be defined only by the preceding illustrative description.

What is claimed is:

1. A system for treating a patient, comprising:
a catheter defining a lumen:
a pusher assembly slidably disposed within the lumen;
a constraining element slidably disposed within the lumen and moveable independently of the pusher assembly, the constraining element having a tubular distal end disposable about a distal portion of the pusher assembly; and
an embolic coil with a proximal end comprising a bulbous element;
wherein the pusher assembly includes a distal receiving element having a first portion defining a first planar surface extending radially and a second portion defining an elongated planar surface extending substantially perpendicular to and distally from the first planar surface, the elongated planar surface having a protrusion extending away from the elongated planar surface;
wherein the first planar surface, the elongated planar surface, and the protrusion are configured to accept at least a portion of the bulbous element; and
wherein the protrusion extends a distance from the elongated planar surface that is less than 50% of a diameter of the bulbous element.

2. The system according to claim 1, wherein an inner diameter of the tubular distal end of the constraining element is not more than 133% of (a) an outer diameter of the bulbous element of the embolic coil plus (b) a thickness of the second portion of the distal receiving element.

3. The system according to claim 1, wherein a combined thickness of the protrusion from the elongated planar surface and the second portion of the distal receiving element is greater than or equal to a difference between the inner diameter of the tubular distal end of the constraining element and a combined thickness of an outer diameter of the bulbous element of the embolic coil and the second portion of the distal receiving element.

4. The system according to claim 1, wherein the bulbous element is connected to the embolic coil by one of a wire and a rod extending axially along a central axis of the coil, and wherein the wire or rod extends axially along a central axis of the embolic coil when the bulbous element and receiving element are engaged and disposed within the lumen of the tubular distal end of the constraining element.

5. The system of claim 1, wherein the constraining element includes a wire or a rod disposed proximally of the tubular distal end, the wire or rod extending parallel to the pusher assembly, and wherein the pusher assembly is disposed coaxially within the catheter lumen.

6. The system of claim 1, wherein the constraining element includes a coiled segment disposed proximally of the tubular distal end, and wherein the pusher assembly is disposed coaxially within a lumen defined by the coiled segment.

7. The system of claim 1, wherein the constraining element includes a wire or a rod disposed proximally of the tubular distal end and disposed coaxially within the catheter lumen, the pusher assembly includes an elongated portion extending parallel to the wire and through a proximal aperture within the tubular distal end.

8. A method of treating a patient, comprising the steps of:
   inserting, into the body of the patient, a catheter defining a lumen and having, slidably disposed within the lumen:
      a pusher assembly including a distal receiving element having a first portion defining a first planar surface extending radially and a second portion defining an elongated planar surface extending substantially perpendicular to and distally from the first planar surface, the elongated planar surface having a protrusion extending away from the elongated planar surface;
      a constraining element slidably disposed moveable independently of the pusher assembly, the constraining element having a tubular distal end disposable about the distal receiving element; and
      an embolic coil with a proximal end comprising a bulbous element engaged with the distal receiving element and the constraining element;
   wherein the protrusion extends a distance from the elongated planar surface that is less than 50% of a diameter of the bulbous element; and
   moving at least one of the pusher assembly and the constraining element relative to the other, thereby permitting the bulbous element to separate from the distal receiving element.

9. The method of claim 8, wherein an inner diameter of the tubular distal end of the constraining element is not more than 133% of (a) an outer diameter of the bulbous element of the embolic coil, plus (b) a thickness of the second portion of the distal receiving element.

10. The method of claim 8, wherein a combined thickness of the protrusion from the elongated planar surface and the second portion of the distal receiving element is greater than or equal to a difference between the inner diameter of the tubular distal end of the constraining element and a combined thickness of an outer diameter of the bulbous element of the embolic coil and the second portion of the distal receiving element.

11. The method of claim 8, wherein the bulbous element is connected to the embolic coil by one of a wire and a rod extending axially along a central axis of the coil, and wherein the wire or rod extends axially along a central axis of the embolic coil when the bulbous element and receiving element are engaged and disposed within the lumen of the tubular distal end of the constraining element.

12. The method of claim 8, further comprising the step of retracting the pusher assembly.

13. The method of claim 12, wherein the constraining element is retracted prior to the pusher assembly.

14. The method of claim 8, wherein the pusher assembly and the constraining element are withdrawn from the catheter, and an assembly and constraining element engaged with a bulbous element of a second embolic coil is reinserted into the catheter.

15. The method of claim 8, further comprising positioning at least part of the embolic coil within a vascular structure to be occluded.

* * * * *